United States Patent [19]

Lindemann et al.

[11] 4,048,992
[45] Sept. 20, 1977

[54] INSUFFLATOR

[76] Inventors: Hans-Joachim Lindemann, Kleiner Schaferkamp 43, 2 Hamburg 6; Peter P. Wiest, Gothaallee 19, 1 Berlin 19, both of Germany

[21] Appl. No.: 624,845

[22] Filed: Oct. 22, 1975

[30] Foreign Application Priority Data

Oct. 26, 1974 Germany .............................. 2451383

[51] Int. Cl.$^2$ ............................................ A61M 16/00
[52] U.S. Cl. ............................ 128/184; 128/DIG. 17; 73/204
[58] Field of Search ................... 128/184, 145.5, 145.6, 128/145.7, 145.8, DIG. 17, DIG. 29, DIG. 13, 188; 73/204

[56] References Cited

U.S. PATENT DOCUMENTS

| | | | |
|---|---|---|---|
| 1,682,344 | 8/1928 | Lesieur | 128/184 |
| 2,831,351 | 4/1958 | Jacobson | 73/204 |
| 2,947,938 | 8/1960 | Bennett | 73/204 |
| 3,289,192 | 11/1966 | Davey | 73/204 |
| 3,557,785 | 1/1971 | McQueen | 128/188 |
| 3,645,133 | 2/1972 | Simeth et al. | 128/DIG. 29 |
| 3,687,130 | 8/1972 | McCormick | 73/204 |
| 3,870,072 | 3/1975 | Lindemann | 128/184 |

Primary Examiner—Robert W. Michell
Assistant Examiner—Henry J. Recla
Attorney, Agent, or Firm—McGlew and Tuttle

[57] ABSTRACT

The insufflator is used for introducing limited quantities of carbon dioxide into the human body for operational purposes, particularly for laparoscopy or hysteroscopy, and is of the type comprising two pressure reducers, in series, followed by a gas flow monitoring device through which carbon dioxide is directed from a gas supply to the human body. The two pressure reducers are constantly adjusted to fixed gas supply pressures, and the monitoring device comprises a cylindrical expansion container having a central inlet port and a large diameter, and in whose peripheral zone the gas flow velocity approaches a zero rate. First and second sensing elements for the measured variable are provided in the expansion container, with the first sensing element being located immediately in the area of the inlet port and the second sensing element being located close to the cylindrical side wall at the maximum possible radial spacing from the first sensing element. The two sensing elements are included in a measuring bridge and a measuring amplifier is connected to the bridge output, with an indicator, of the rate of gas flow per unit of time, being connected to the amplifier output. For laparoscopy, the second pressure reducer is adjusted to a gas supply pressure of 15 mm Hg, and the expansion container is followed by a precision needle valve adjustable in the range of zero to 2 liters per minute. For hysteroscopy, the second pressure reducer is constantly adjusted to a supply pressure of 200 mm Hg and the expansion container is followed by a precision aperture limiting the maximum gas flow to 100 ml/min.

4 Claims, 4 Drawing Figures

INSUFFLATOR

BACKGROUND OF THE INVENTION

The present invention relates to an insufflator for introducing limited quantities of carbon dioxide into the human body for operational purposes, particularly laparoscopy, comprising two pressure reducers followed by a gas flow monitoring device through which the carbon dioxide is directed to the body from the gas supply. For a gentle enlargement of body cavities, particularly in laparoscopy, but also in the hysteroscopy, it is usual to insufflate carbon dioxide into the human body, under a pressure which is adapted to the given conditions. In laparoscopy, a Verres needle is connected to the insufflator by means of a flexible tubing and, in the hysteroscopy, a hysteroscope is connected.

In a known insufflator of the mentioned kind, the gas flow monitoring device comprises a vertically extending glass tube which is mounted outside the insufflator and accommodates a floating ball which is vertically movable under the action of the gas stream. The device is used, in connection with a pressure gage and a pressure reducer switchable automatically or manually, for checking the carbon dioxide quantity supplied by the insufflator. With a manual actuation of the pressure reducer, the admissible intraabdominal pressure may be substantially exceeded so that, upon a possible wrong actuation of such an insufflator, a pressure level may be adjusted which is dangerous to the life the patient. For example, this may occur when the pressure reducer has been switched to hand operation and an attempt is made to determine the probable position of the Verres needle according to the indication of the pressure gage and the position of the floating ball. Evidently, and this is exactly the criterion of security, in case of an erroneous actuation, i.e., without having switched the pressure reducer to automatic operation, the patient is not sufficiently protected.

SUMMARY OF THE INVENTION

The present invention is directed to an insufflator of the mentioned kind insuring an absolute security of the treated patient and permitting an exact measurement of the gas stream passing therethrough while making sure that the gas pressure does not exceed the admissible intraabdominal pressure.

The design in accordance with the invention is such that the pressure reducers are constantly adjusted to fixed gas supply pressures, and that the gas flow monitoring device comprises an expansion container having a large diameter so that, in the peripheral zones, the gas flow velocity approaches the value zero. Within the expansion container, sensing elements for the measured variable are provided, of which one is located directly at the inlet port of the expansion container and the other located close to the peripheral wall of the expansion container at a distance as large as possible from the first sensing element. The two sensing elements form a part of a measuring bridge to the output of which a measuring amplifier is connected which is followed by an indicator of the rate of gas flow per unit of time.

Due to the pressure reducers fixedly adjusted to constant supply pressures, not only is there obtained security that the supply pressure of the insufflator never exceeds the admissible intraabdominal pressure so that the inventive insufflator operates without any danger, but, in addition, an exact measuring, independent of the pressure, of the gas quantity flowing through per unit of time is made possible by means of the gas flow monitoring device designed in accordance with the invention. This device, comprising the expansion container, the two sensing elements located within the expansion container and connected to the measuring bridge, as well as the measuring amplifier followed by the indicator section, operates independently of the temperature and pressure, so that the rate of flow of the gas is indicated exactly. In addition, if in accordance with the invention an indicating integrator following the measuring amplifier is provided for determining the total gas flow, the probable position of the point of the Verres needle connected to the insufflator can be exactly concluded. In addition, the inventive insufflator is capable of automatically controlling the supplied quantity of gas so that a constant volume of gas is maintained in the abdominal cavity under an admissible pressure which is adjusted at the pressure reducers.

In a further advantageous development of the invention intended for laparoscopy, the second pressure reducer followed by following the first one is permanently adjusted to a gas supply pressure of 15 mm Hg. This corresponds to the admissible intraabdominal pressure which, in laparoscopy, is in accordance with the most recent scientific knowledge. The first pressure reducer reduces the pressure of about 60 bars, present in a conventional carbon dioxide gas cylinder, to 1.5 bar, while the following second pressure reducer reduces the pressure of 1.5 bar to the gas supply pressure of 15 mm Hg. Another development of the invention provides a precision needle valve which is mounted downstream of the expansion container and is adjustable to a gas supply in the range of zero to 2 liters per minute.

According to a still further development of the invention, the expansion container comprises a cylindrical part and two end plates which are provided with circular grooves into which the cylindrical part is hermetically secured. Connection pieces for the gas conduit are centrically received in the two end plates.

While using the inventive insufflator in hysteroscopy, the pressure reducer mounted downstream is permanently and fixedly adjusted to a gas supply pressure of 200 mm Hg admissible in this case and the expansion container is followed by a precision aperture limiting the maximum gas flow to 100 ml/min. By using an insufflator thus equipped in hysteroscopy, the danger of an embolism occurring in the human body during the insufflation is eliminated. The danger of a gas embolism appears in cases where the quantity of gas introduced into the human body within a certain period of time is so large that the dissolving capacity of the blood is exceeded so that gas bubbles may form in the main vein of the heart, with possible fatal consequences.

An object of the invention is to provide an improved insufflator for introducing limited quantities of carbon dioxide into the human body for operational purposes.

Another object of the invention is to provide such an insufflator insuring an absolute security of the treated patient.

A further object of the invention is to provide such an insufflator permitting an exact measurement of the gas stream passing therethrough while insuring that the gas pressure does not exceed the admissible interabdominal pressure.

Yet another object of the invention is to provide such an insufflator including two pressure reducers in series followed by a novel monitoring device, with the pressure reducers constantly adjusted to fixed gas supply pressures and the monitoring device comprising an expansion container having a large diameter so that, in its peripheral zones, the gas flow velocity approaches a zero rate of flow.

A further object of the invention is to provide such an insufflator which operates independently of the temperature and pressure so that the rate of flow of the gas is indicated exactly.

For an understanding of the principles of the invention, reference is made to the following description of a typical embodiment thereof as illustrated in the accompanying drawings.

DESCRIPTION OF THE PREFERRED EMBODIMENT

Figure 2:
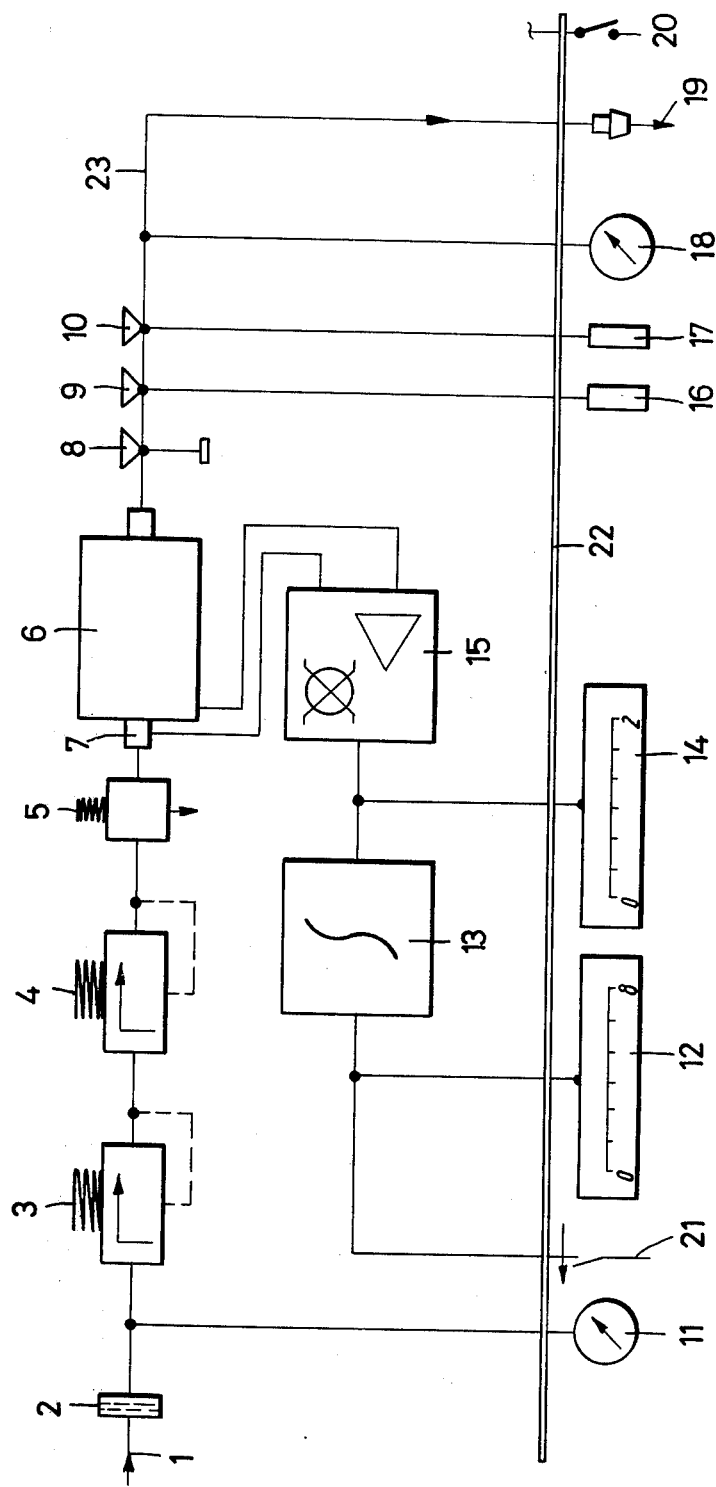
FIG. 2 is a diagrammatical illustration of the gas flow through the insufflator.
Figure 4:
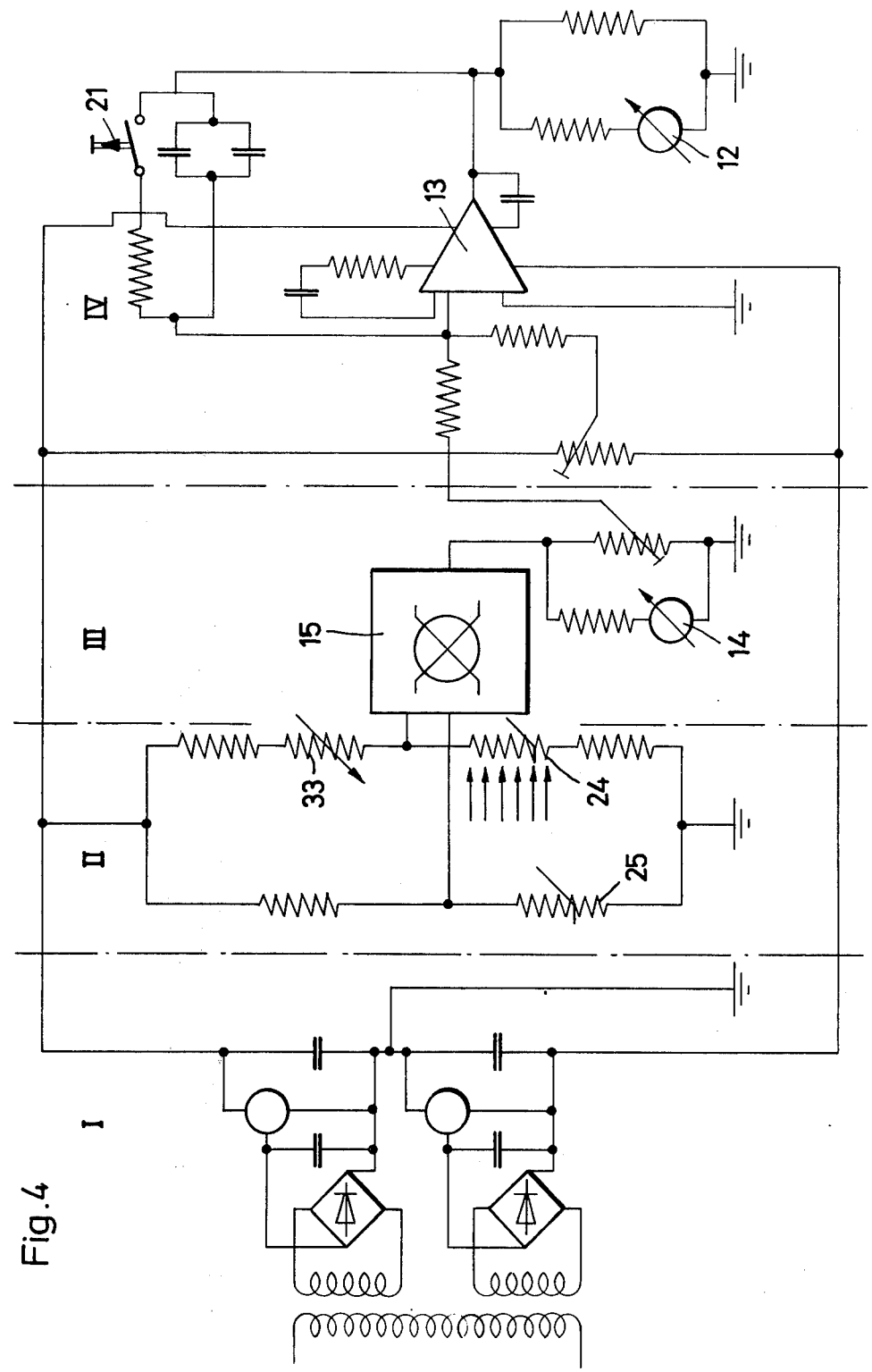
FIG. 4 is a circuit diagram of the electrical part of the insufflator.

Referring to FIG. 2 of the drawings, the insufflator comprises a part conveying the carbon dioxide, and an electrical measuring part, shown in FIG. 4. The part conveying the carbon dioxide comprises a connection 1 for a conventional carbon dioxide gas cylinder, a filter 2, a first pressure reducing stage 3 reducing the primary pressure of about 60 bar present in the carbon dioxide gas cylinder to a secondary pressure of 1.5 bar, a second pressure reducing stage 4 reducing the primary pressure of 1.5 bar to a secondary pressure of 15 mm Hg, an excess-pressure safety valve 5, an expansion container 6 forming a part of a gas flow monitoring device, a precision aperture 8 permanently adjusted to the maximum rate of flow, a valve 9 for switching the insufflation on and off, and an adjustable precision needle valve 10.

Figure 1:
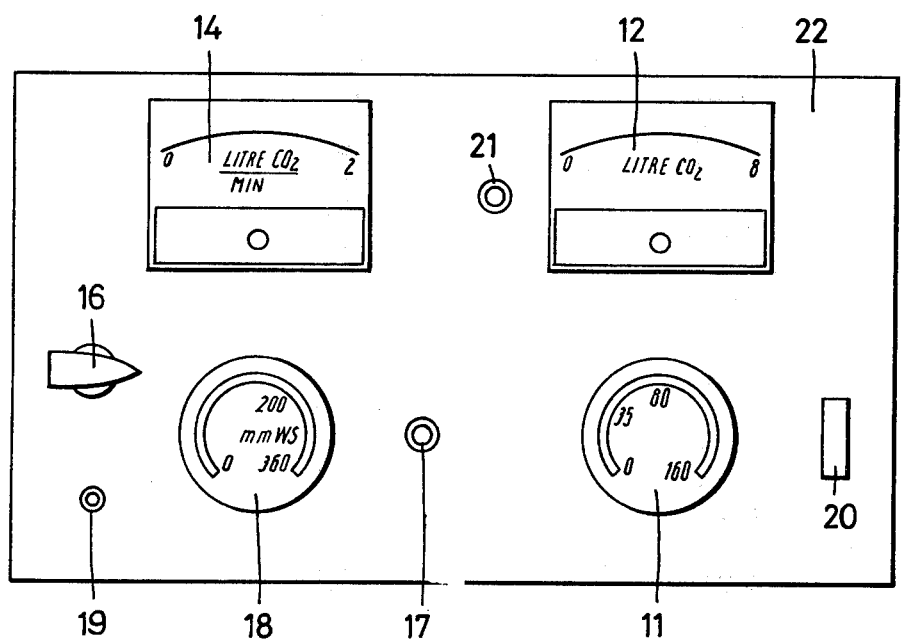
FIG. 1 is an elevational view of the front panel of the insufflator.

All the just mentioned parts are accommodated in a housing 22 the front panel of which is shown in FIG. 1 in elevation and corresponds to the diagrammatical showing of FIG. 2, and are connected to one another through a gas flow conduit 23. Between filter 2 and the first pressure reducer 3, a branched line leads to a pressure gage 11 which is mounted on the front panel of housing 22 and indicates the pressure of the carbon dioxide gas cylinder. Another branched line leads to a pressure gage 18 indicating the actual pressure in the body cavity of the patient. Gas line 23 further leads to an outlet nipple 19 which is also mounted on the front panel of housing 22 and intended for being connected to a laparoscope. Valves 9 and 10 are actuable by means of rotary knobs 16, 17 provided on the front panel of housing 22. A power switch 20 serves for switching the operational voltage of the insufflator on and off.

Expansion container 6 comprises a measuring equipment 7 including sensing elements 24, 25 for the measured variable. As shown diagrammatically in FIG. 2, the elements are connected to an amplifying unit 15 having a power section and a measuring section. Amplifying unit 15 delivers a signal indicating the rate of flow per unit of time which may be read on an electric indicator 14 having a scale graduated from 0 to 2 liters of gas per minute. By means of an integrator 13 diagrammatically shown in FIG. 2, the total flow of carbon dioxide is determined and indicated on an electric indicator 12 having a scale graduated from 0 to 8 liters of carbon dioxide. A key 21 is provided for zeroing the indication of the total flow. Parts 12, 14 and 21 are also mounted on the front panel of housing 22 as shown in FIG. 1.

Figure 3:
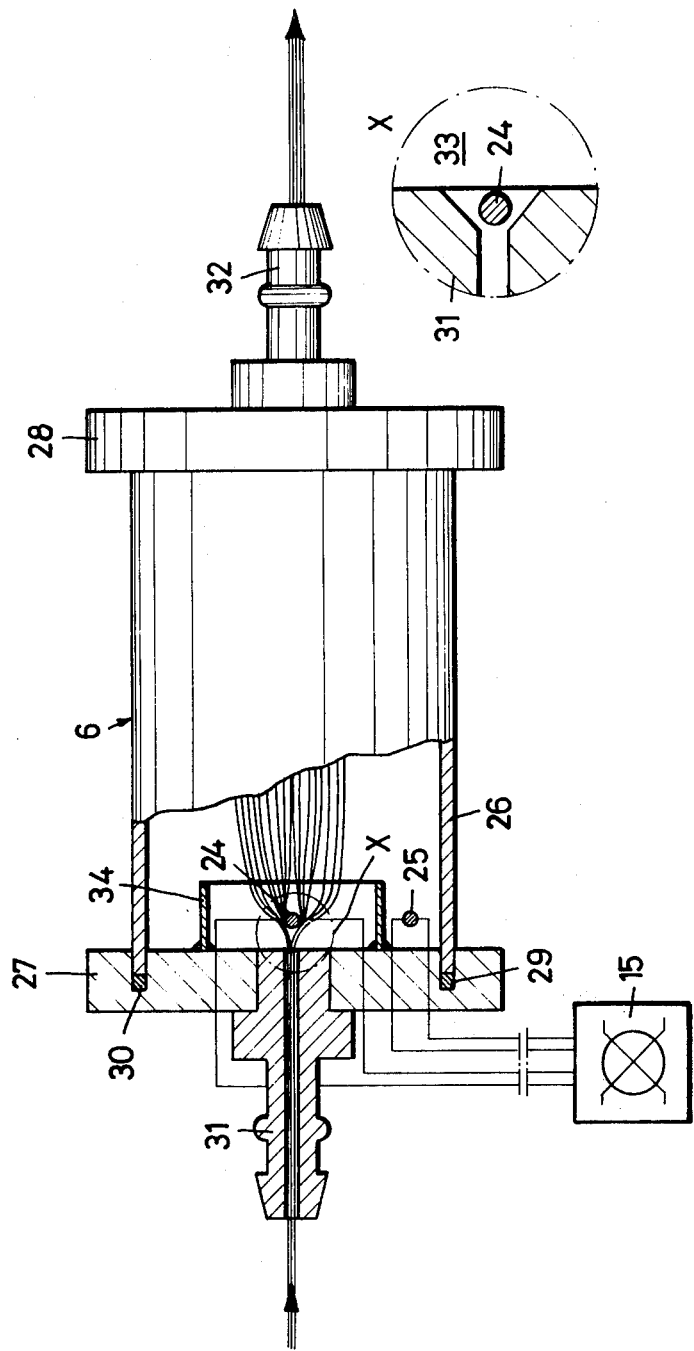
FIG. 3 shows the gas flow monitoring device of the insufflator in an enlarged side elevation view, partly in section.

Expansion container 6 is shown in FIG. 3 approximately in actual size and comprises a cylindrical part 26 and two end plates 27, 28 which are provided with circular grooves 29 into which cylindrical part 26 is hermetically engaged with gaskets 30 interposed. Connecting pieces 31, 32 are centrically received in both end plates 27, 28. The connecting pieces are provided with an outer ribbing for establishing connection with gas conduit 23. By means of tie rods (not shown) extending outside the cylindrical part and parallel to the axis thereof, end plates 27, 28 are connected to each other. Expansion container 6 has a diameter which is much larger than the diameter of gas conduit 23 so that, in the internal peripheral zones of container 6, the velocity of the gas flow approaches the value zero. Of the two sensing elements 24, 25 accommodated in expansion container 6, element 24 is mounted directly in the area of the inlet port of connecting piece 31 as shown in detail X of FIG. 3 so that the carbon dioxide stream passes therearound. The other sensing element 25 is mounted near the wall of the cylindrical part of expansion container 6 at the largest possible radial spacing from sensing element 24 so that, in the zone of sensing element 25, the flow velocity of the gas drops almost to zero. To direct the gas stream, a cylindrical metal screen 34 is provided concentrically surrounding the inlet port. The indicated electric leads from sensing elements 24, 25 to amplifying unit 15 are passed through expansion container 6 in an insulated and gastight manner.

The two sensing elements 24, 25 are made of an NTC material and form a part of a measuring bridge II which comprises further fixed resistances and an adjustable resistor 33. The alternating electric current supplied to power section I from a source (not shown) is rectified and the resulting unidirectional current flows through the two sensing elements 24, 25 which have similar characteristics so that they are maintained at the same temperature level. As long as the ambient medium of the resistors and sensing elements 24, 25 is at rest, the measuring bridge is balanced, i.e., the voltage delivered to the amplifier 15, provided in indicator section III, is zero. However, as soon as the gas stream to be measured flows past sensing element 24 while, in the vicinity of sensing element 25, the same gas medium is stagnant, the measuring bridge becomes unbalanced. Although the two sensing elements 24, 25 are heated with an approximately constant wattage, the gas stream flowing past sensing element 24 reduces the conductivity thereof. In spite of the constant energy supply, the temperature of the sensing element drops, its resistance increases and the measuring bridge becomes unbalanced, i.e., a voltage is applied to amplifier 15. Sensing element 25, located in the stagnant medium, serves to make the measurement independent of the temperature. The zero point of the measuring bridge does not vary with the ambient temperature since it can be assumed that the initial temperature is the same for both sensing elements 24, 25.

Starting from the assumption that, at both of the sensing elements 24, 25, the carbon dioxide has the same temperature, only the velocity of the fluid flowing past sensing element 24 remains as the determining factor for the variation of the resistance. The condition is, however, that one of the sensing elements must be located in the stagnant part of the medium, which is insured by the design of the expansion container 6 and the location of sensing element 25. The gas stream flowing around sensing element 24 changes the electrical resistance thereof in accordance with the rate of flow of the gas, since an NTC resistor is temperature responsive.

NTC resistors (having a negative temperature coefficient) are electric resistors which are also called hot conductors. They are made of ceramic materials and their resistance behavior is just the inverse of the resistance behavior of metals. That is, with increasing temperature, the resistance of NTC resistors decreases very strongly. Already at small temperature variations, the NTC resistors show high variations of resistance so that the ratio of the resistance to temperature variation is very large. In NTC resistors, the variation of resistance is not accompanied by hysteresis. With a high temperature coefficient, the operational or self temperature may be relatively low. At the same time, the amplification of the signal delivered by the NTC resistor may also be small, which considerably increases the security against disturbances and results in relatively low expenses. Since they are small in size and their operational temperature is low, NTC resistors can be accommodated without problems.

Another condition for an exact measurement is a constant pressure, which is insured by the fixedly adjusted pressure reducers 3, 4. In a stagnant ambience, i.e., as long as there is no gas flow, and with a constant energy supply, sensing element 25 has a definite operational temperature. An equilibrium is established between the supply of electric energy and the transmission of heat to the ambient medium. As soon as a fluid flow is adjusted, the heat transmission to the ambient medium increases correspondingly. A new equilibrium is established at a lower operational temperature of the sensing element, and the electric resistance changes analogously. As mentioned above, the sensing element 25, located in the stagnant medium, serves to make the measurement independent of the temperature and pressure. The usual evaluation of signals, however, leads to an error in measurement which is too large for medical purposes. That is, since the carbon dioxide drawn from the gas cylinder expands, stable temperature conditions are never obtained. To compensate this drawback, the signal coming from measuring bridge II is picked up only from a following electronic circuit in which amplifier 15 is provided. This circuit forms a quotient of the two sensing element currents. While forming the quotient, the variables, i.e., the temperature and pressure of the gas, which influence the measurement result negatively, are cancelled, so that only a quotient of the two currents flowing through sensing elements 24, 25 is obtained.

Due to the continuous electronic determination of the resistance variations of sensing element 24, which is located in the flowing gas, the rate of flow per unit of time through gas conduit 23, after an appropriate linearization, is indicated on the graduated electric indicator 14.

For laparoscopy, it is necessary also to know the total flow of carbon dioxide. For this purpose, a partial voltage of the output signal of amplifier 15 is shunted and applied to the input of an integrator circuit IV comprising the integrator 13. The signal received fom the integrator and indicated on the electric indicator 12 is proportional to the total gas volume which has passed through an expansion container 6. By actuating key 21, indicator 12 for the total flow can be zeroed before starting a new measurement. The rate of flow can be adjusted, with the precision needle valve 10, from the front panel of housing 22. The adjusted rate of flow may be read on indicator 14. Depending on the conducting capability of the Verres needle, which may vary because of a possible wear or contamination, a back pressure builds up with the predetermined insufflated gas volume in front of the point orifice of the Verres needle. This back pressure can be read on pressure gage 18. Since the operation of the Verres needle is only volume-limiting and not pressure-limiting, it is only a function of time, with a simultaneous dependence of the produced volume, until the maximum pressure of insufflator, i.e., in laparoscopy, the pressure of 15 mm Hg, becomes equal to the pressure of the gas bubble in the abdominal cavity. As soon as a pressure equilibrium is achieved, i.e., the pressure difference is equal to zero, the indicator 14 also indicates a zero rate of flow. Upon reading the total flow on indicator 12 mounted on the front panel, a quantitative conclusion can be drawn about the size of the gas bubble formed in the patient's body.

These actual possibilities of indication and monitoring, along with the simultaneous determination of the probable position of the Verres needle point, make the laparoscopic method using the inventive insufflator quite harmless for the patient. A pressure increase for determining the point position is not necessary, since the data crucial for the position of the Verres needle, i.e., the rate of gas flow, the total gas flow from the beginning up to the instant of reading, and the actual pressure of the gas bubble within the body, can be exactly read on the device.

Upon reaching the state of equilibrium, indicator 14 for the rate of flow per unit of time indicates zero. The actual pressure within the patient's body has increased to 15 mm Hg and the total gas flow can be read on the graduated indicator 12.

For using the insufflator described in the foregoing in hysteroscopy, the embodiment, otherwise largely corresponding to the first one, must be modified. The difference consists only in replacing the second pressure reducer 4 by a pressure reducer producing a fixed and constant gas supply pressure of 200 mm Hg. At the same time, the fixedly adjusted precision aperture 8, following the expansion container 6, must be limited to a maximum gas flow of 100 ml/min. Integrator 13 and indicator 12 may be omitted or, instead of indicator 12, a recorder may be provided. Indicator 12 may also be provided along with an additional recorder.

It is evident that the insufflator described in this specification may also be used for other gases employed in medical practice. Finally, it has been found that the above described gas flow monitoring device can be used with particular advantages also in the general technological field for measuring gas flows. To this effect, the mentioned gas flow monitoring device is used as a separate constructional unit substantially comprising the expansion container 6 with the two sensing elements 24, 25, the measuring bridge II, the amplifier 15 with the indicator 14 and, selectively, the integrator 13 with the indicator 12, in addition. The particular advantage of this separate gas flow monitoring device is based on the exact measuring of the gas flow.

While a specific embodiment of the invention has been shown and described in detail to illustrate the application of the principles of the invention, it will be understood that the invention may be embodied otherwise without departing from such principles.

What is claimed is:

1. In an insufflator for introducing limited quantities of carbon dioxide into the human body for operational purposes, particularly for laparoscopy of the type including an inlet for connection to a source of carbon dioxide under pressure, an adapter connection for medical instruments, particularly, laparascopes and hysteroscopes, insertable in the human body, and pressure regulator means connected in series to the inlet and followed by a gas flow monitoring device, and through which, in series, the carbon dioxide is directed from the gas supply to the adapter connection, the improvement comprising, in combination, said pressure regulator means being constituted by two pressure regulators connected in series between said inlet and said flow-monitoring device and constantly adjusted to respective fixed gas supply pressures; said monitoring device comprising an expansion container having end and side walls with an inlet port located centrally of one end wall and an outlet port located centrally of the other end wall, the expansion container having a large cross-sectional area perpendicular to the flow direction therethrough, and having a peripheral zone spaced laterally from said inlet and outlet ports in which the gas flow velocity approaches a zero rate; sensing elements, providing currents corresponding to a measured variable of the gas flow, provided in said expansion container and including first sensing element located immediately in the area of said inlet port, and subjected to the gas flow, and a second sensing element located in said peripheral zone close to the side wall of said container at the maximum possible lateral spacing from said first element; a flow-directing cylindrical screen surrounding said first sensing element and shielding said second sensing element from the gas flow through said inlet port to said outlet port; a precision aperture, permanently adjusted to the maximum rate of flow, connected in series following said outlet port; an adjustable precision needle valve following said precision aperture; a pressure gauge connected to said adapter connection to indicate the back pressure at said adapter connection; a measuring bridge including said first and second sensing elements and having an input and an output; a source of electrical potential connected to the input of said measuring bridge; a measuring amplifier having an input connected to the bridge output and deriving the quotient of the respective currents of said first and second sensing elements, and having an output; an indicator, of the rate of gas flow per unit of time, connected to the amplifier output; the rate of flow being adjustable by said precision needle valve in accordance with the reading of said indicator; an integrator connected to the output of said amplifier; and a second indicator, for indicating the total gas flow, connected to said integrator, whereby the reading of said second indicator permits the drawing of a quantitative conclusion as to the size of the gas bubble in the human body.

2. In an insufflator, the improvement claimed in claim 1, in which, for laparoscopy, the downstream pressure reducer following the upstream pressure reducer in series therewith is adjusted to a gas supply pressure of 15 mm Hg.

3. In an insufflator, the improvement claimed in claim 2, in which said precision needle connected to the outlet port of said expansion container is adjustable within the range of zero to 2 liters per minute.

4. In an insufflator, the improvement claimed in claim 1, in which, for hysteroscopy, the downstream pressure reducer following in series the upstream pressure reducer is constantly adjusted to a fixed gas supply pressure of 200 mm Hg; said precision aperture connected to the outlet port of said expansion container limiting the maximum gas flow to 100 ml/min.

* * * * *